(12) United States Patent
Hauri et al.

(10) Patent No.: US 8,251,961 B2
(45) Date of Patent: *Aug. 28, 2012

(54) SAFETY NEEDLE ASSEMBLY AND METHOD FOR MAKING THE SAME

(75) Inventors: Marius Hauri, Westmoreland, NH (US); Frank Blinkhorn, Keene, NH (US); David Maclean, Swanzey, NH (US); Lawrence P. Hudon, Hinsdale, NH (US); Robert Simas, Jr., Keene, NH (US); Troy M. Derby, Stoddard, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 1312 days.

This patent is subject to a terminal disclaimer.

(21) Appl. No.: 10/665,514

(22) Filed: Sep. 22, 2003

(65) Prior Publication Data

US 2005/0065481 A1 Mar. 24, 2005

(51) Int. Cl.
*A61M 5/00* (2006.01)
(52) U.S. Cl. ........................................ 604/263
(58) Field of Classification Search ............... 604/181, 604/192, 198, 240–243, 263
See application file for complete search history.

(56) References Cited

U.S. PATENT DOCUMENTS

| | | | |
|---|---|---|---|
| 2,693,183 A * | 11/1954 | Lockhart | 604/201 |
| 4,664,259 A | 5/1987 | Landis | |
| 4,982,842 A | 1/1991 | Hollister | |
| 5,037,401 A | 8/1991 | DeCamp | |
| 5,139,489 A | 8/1992 | Hollister | |
| 5,154,285 A | 10/1992 | Hollister | |
| 5,188,611 A | 2/1993 | Orgain | |
| 5,232,454 A | 8/1993 | Hollister | |
| 5,277,311 A | 1/1994 | Hollister | |
| 5,445,619 A * | 8/1995 | Burns | 604/192 |
| 5,490,841 A * | 2/1996 | Landis | 604/110 |
| 5,509,907 A | 4/1996 | Bevilacqua | |
| 5,584,816 A | 12/1996 | Gyure et al. | |
| 5,599,313 A | 2/1997 | Gyure et al. | |
| 5,599,318 A | 2/1997 | Sweeney et al. | |
| 5,632,732 A | 5/1997 | Szabo et al. | |
| 5,643,219 A | 7/1997 | Burns | |
| 5,662,617 A | 9/1997 | Odell et al. | |
| 5,665,075 A | 9/1997 | Gyure et al. | |
| 5,669,889 A * | 9/1997 | Gyure et al. | 604/263 |
| 5,681,295 A * | 10/1997 | Gyure et al. | 604/263 |
| 5,697,908 A | 12/1997 | Imbert et al. | |
| 5,733,265 A | 3/1998 | Bachman et al. | |
| 5,868,716 A | 2/1999 | Sweeney et al. | |
| 5,891,103 A | 4/1999 | Burns | |
| 5,913,846 A | 6/1999 | Szabo | |
| 5,919,165 A | 7/1999 | Benson | |
| 5,993,426 A | 11/1999 | Hollister | |

(Continued)

*Primary Examiner* — Kevin C Sirmons
*Assistant Examiner* — Michael J Anderson
(74) *Attorney, Agent, or Firm* — Louis Woo

(57) ABSTRACT

A safety needle assembly has a needle hub and a collar. Integrally formed from the proximal portion of the needle hub is a ring that surrounds its luer base. At the distal portion of the needle hub there are coaxially formed circumferential flanges which act to allow the collar to be rotatable about the needle hub. A needle protection housing is connected to the collar and is pivotable to cover the needle that extends from the distal end of the needle hub. Before use, the needle extending from the needle hub is covered by a needle sheath that has a groove formed circumferentially at its proximal end that snap-fits to a circumferential rib formed at the distal end of the collar.

25 Claims, 7 Drawing Sheets

U.S. PATENT DOCUMENTS

| | | |
|---|---|---|
| RE37,110 E | 3/2001 | Hollister |
| RE37,252 E | 7/2001 | Hollister |
| 6,328,713 B1 | 12/2001 | Hollister |
| 6,334,857 B1 | 1/2002 | Hollister |
| 6,440,104 B1 | 8/2002 | Newby et al. |
| 6,719,737 B2 | 4/2004 | Kobayashi |
| 7,014,622 B1 * | 3/2006 | Pressly et al. .............. 604/110 |
| 7,156,825 B2 * | 1/2007 | Hudon .......................... 604/192 |
| 2002/0010433 A1 * | 1/2002 | Johnson et al. ............... 604/241 |
| 2002/0161336 A1 * | 10/2002 | Crawford et al. ............. 604/192 |

* cited by examiner

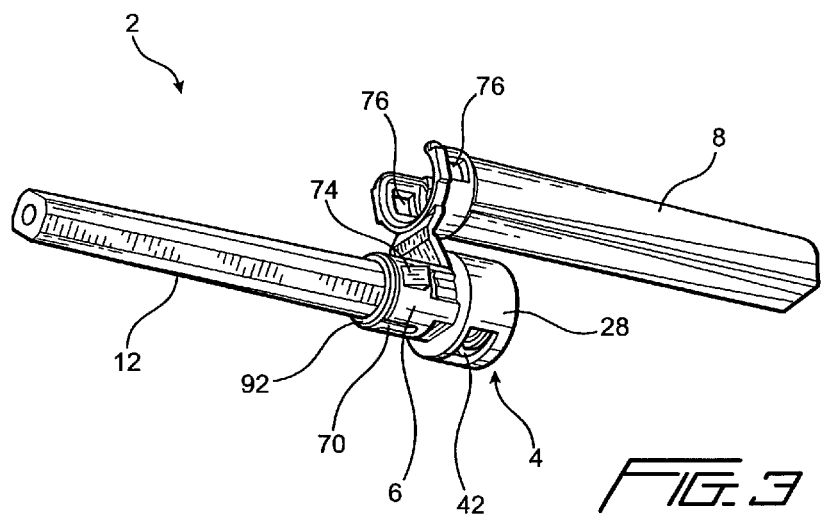
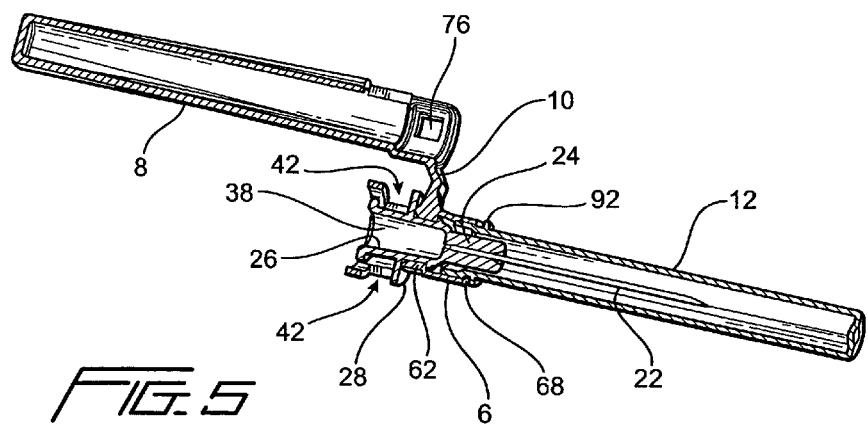

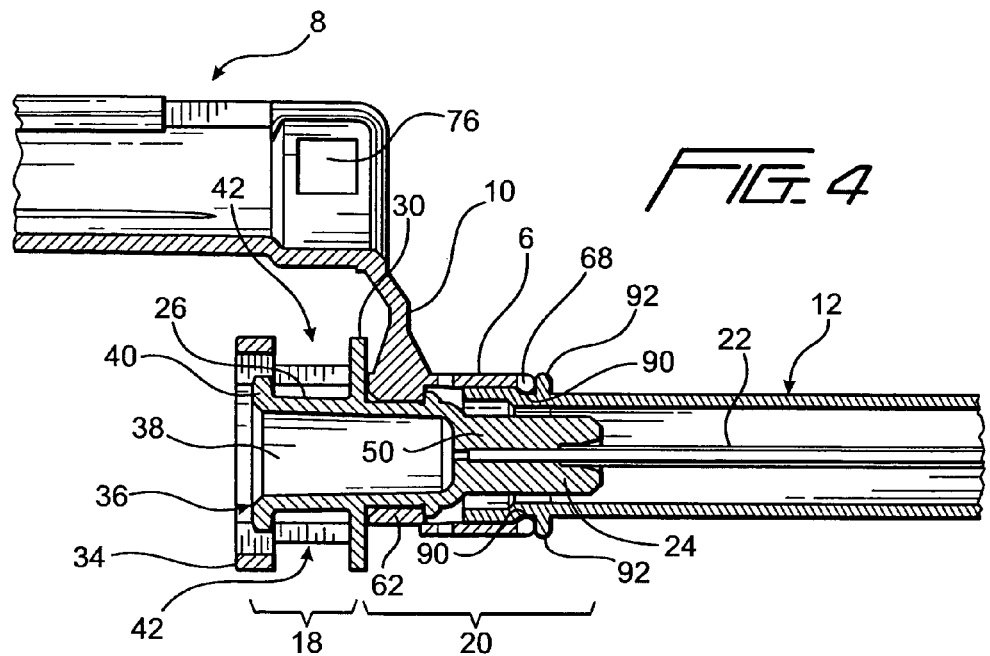
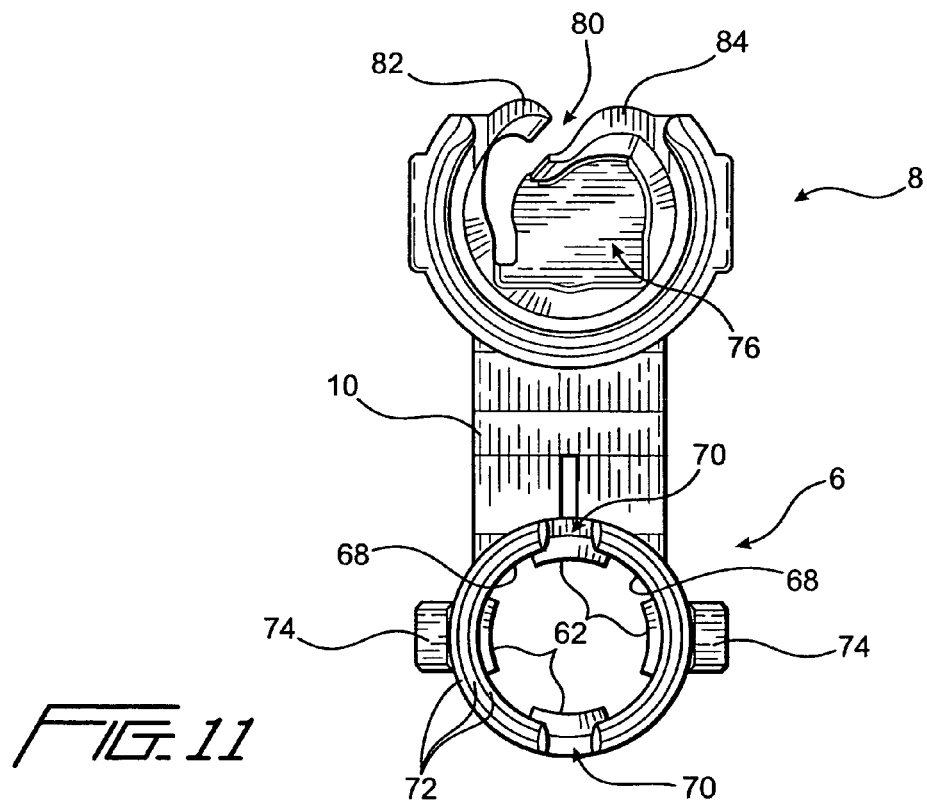

SAFETY NEEDLE ASSEMBLY AND METHOD FOR MAKING THE SAME

CROSS REFERENCE TO RELATED APPLICATIONS

The instant invention is related to the invention disclosed in the application entitled "Needle Protection Assembly" U.S. application Ser. No. 10/649,837 now U.S. Pat. No. 7,201,736 filed on Aug. 27, 2003. The disclosure of the related application is incorporated by reference to this application.

FIELD OF THE INVENTION

The present invention relates to needles and more particularly a safety needle assembly in which the needle sheath for protecting the needle prior to use is attached to a collar rotatably mounted about the needle hub of the needle assembly.

BACKGROUND OF THE INVENTION

There are a number of needle protection devices disclosed in the prior art. Among them are a number of patents assigned to the same assignee as the instant invention. Without limitations, some of those patents are: U.S. Pat. Nos. 4,982,842; 5,139,489; 5,154,285; 5,232,454; 5,277,311; 5,993,426; 6,328,713; 6,334,857; U.S. Pat. No. RE37,110 and U.S. Pat. No. RE37,252. Some other patents that describe needle protection devices, or parts thereof, include U.S. Pat. Nos. 4,664,259; 5,037,401; 5,171,303; 5,188,611; 5,490,841; 5,509,907; 5,584,816; 5,599,313; 5,599,318; 5,632,732; 5,643,219; 5,662,617; 5,665,075; 5,669,889; 5,681,295; 5,697,908; 5,733,265; 5,868,716; 5,891,103; 5,913,846; 5,919,165 and 6,440,104.

The needle protection assembly of the instant invention is made up of parts that are radically different from the prior art, as exemplified by the above-noted patents.

SUMMARY OF THE PRESENT INVENTION

The safety needle assembly of the instant invention is designed to enable a user to connect the needle hub to a medical device, such as for example a syringe, by grasping the needle hub proper, thereby ensuring a more secure fit to the syringe. Unlike the prior art needle assemblies, the sheath that covers the needle plays no part in the securing of the needle hub to the medical device.

The needle hub is especially designed to have a ring surrounding the luer end of the hub to allow a user to grasp this ring to couple the needle hub to the medical device. The ring is an integral part of the needle hub and it has a distal wall that extends orthogonally from a proximal portion of the main body of the hub, with the body of the ring extending rearward to cover the luer end of the needle hub that couples to a corresponding luer of the medical device. The circumferential side wall of the ring is spaced from the luer of the needle hub. The proximal end of the ring is open to allow the mating of the luer of the needle hub to the corresponding luer of the medical device. To enable the user to see the initial blood flash so as to determine whether the needle has correctly been inserted into the vein of a patient during blood drawing, windows are provided at the sidewall of the ring to allow the user to have a clear view of the luer body, and the luer end.

The needle hub has at its distal portion a number of flanges formed along a circumferential axis. The flanges are chamfered at their respective surfaces that face the needle extending from the distal end of the needle hub. The back surfaces of the flanges are flat for defining a space between the flanges and the distal wall of the ring circumferentially formed about the distal portion of the needle hub.

A collar to which a needle protection housing is attached is fitted to the space defined by the flanges and the distal wall of the ring on the needle hub. To facilitate the fitting, a number of internal protrusions or bosses are provided at the proximal end of the collar. The respective surfaces of the protrusions that come into contact with the flanges at the needle hub are also chamfered to facilitate the mating of the collar to the needle hub. The back end of the substantially rectangular protrusions are flat, so that once the collar is fitted to the needle hub, it could not be removed therefrom.

At the distal portion of the collar there is formed a circumferential internal rib. Slots are also provided at the distal portion of the collar to enable the flexing of the distal end of the collar for the insertion and removal of a needle sheath that removably couples thereto.

The collar has pivotally or hingedly attached thereto a housing which is pivotable to the direction along a longitudinal axis of the needle hub for covering the needle after use. Formed substantially along the length of the housing is an opening that is off centered. The opening is formed by two lips or flaps that extend substantially along the length of the housing, with the first or upper lip overlapping the second or lower lip. The respective lips each are angled toward the interior of the housing, but with varying angles along the lengths of the lips. As a consequence, when the housing is pivoted to cover a used or contaminated needle, the needle would enter into the housing guided by the lips at angles that ensure that it smoothly enters into the housing, thereby preventing flickering of any contaminated fluid that may have adhered to the needle. The lips, particularly the lower lip, are designed such that, once fully enters into the housing, the needle is prevented from escaping from the housing. For added safety, respective portions of a locking mechanism are provided at the base portion of the housing and the outer surface of the distal portion of the collar.

The needle sheath that covers the needle prior to use has a notch or groove formed circumferentially proximate to its open end. During manufacturing of the needle assembly, the needle sheath is placed or positioned over the needle and moved along the longitudinal axis of the device to mate with the distal portion of the collar mounted about the needle hub. With a predetermined force, the needle sheath is coupled to the collar, with the rib at the distal end of the collar fitting into the groove formed at the proximal end of the needle sheath.

To remove the safety needle assembly of the instant invention from the medical device, the user would grasp the ring of the needle hub and rotate the needle assembly in a rotational movement that is counter to the rotational movement used to couple the needle assembly to the medical device, if the coupling of the needle assembly to the medical device is via luer lock coupling. If it is a luer fit coupling, then the user would pull the needle assembly away from the medical device.

BRIEF DESCRIPTION OF THE FIGURES

The present invention will become apparent and the invention itself will be best understood with reference to the following description of an embodiment of the present invention taken in conjunction with the accompanying drawings, wherein:

FIG. 2 is a perspective view showing the various components of the safety needle assembly of FIG. 1 and a medical device such as a conventional needle syringe to which the safety needle assembly of the instant invention is used with;

FIG. 3 is a perspective view of the safety needle assembly of the instant invention with all of the components assembled;

FIG. 4 is a cross-sectional view of the safety needle assembly of the instant invention;

FIG. 5 is a perspective cross-sectional view of the needle assembly of the instant invention;

FIG. 11 is a plan view of the needle protection housing and the collar component of the safety needle assembly of the instant invention;

DETAILED DESCRIPTION OF THE INVENTION

Figure 1:
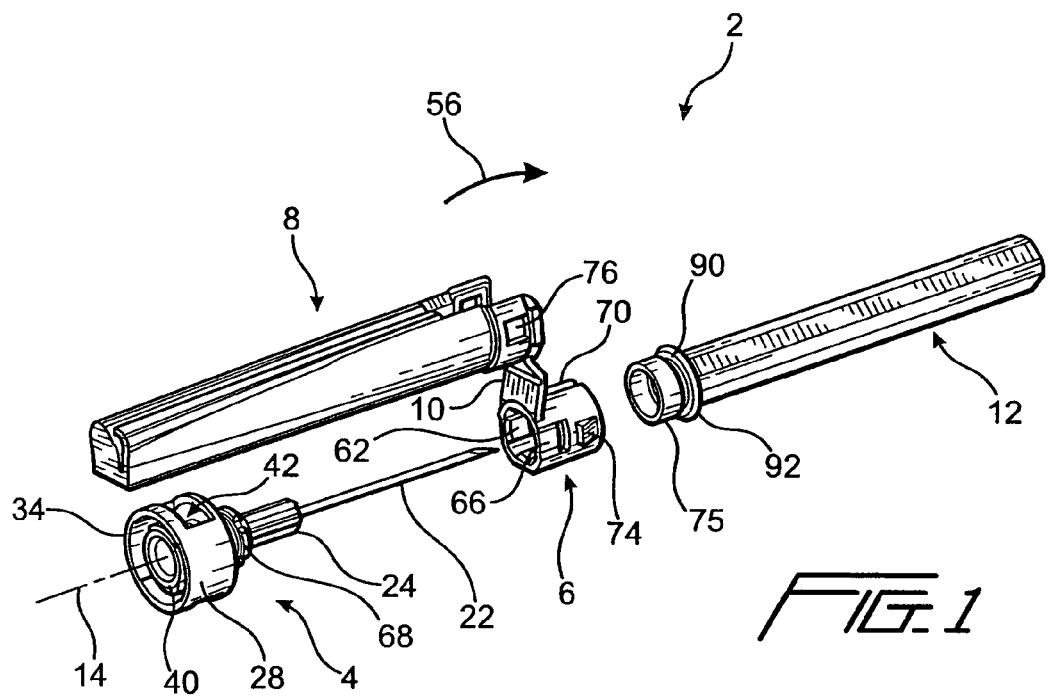
FIG. 1 is a perspective view showing the different component parts of the safety needle assembly of the instant invention.

With reference to FIG. 1, the safety needle assembly 2 of the instant invention is shown to comprise four major components, namely a needle hub 4, a collar 6, a needle protection housing 8 attached to the collar 6 via a living hinge 10, and a needle sheath 12. As shown, needle hub 4, collar 6 and needle sheath 12 are in alignment along a longitudinal axis 14. The exposed components of the safety needle assembly of the instant invention are further shown in FIG. 2 to be in alignment with a conventional syringe 16 with a luer lock receptacle end that mates with needle hub 4. An assembled safety needle assembly of the instant invention is shown in perspective view in FIG. 3 and in cross-sectional views in FIGS. 4 and 5.

Figure 6:
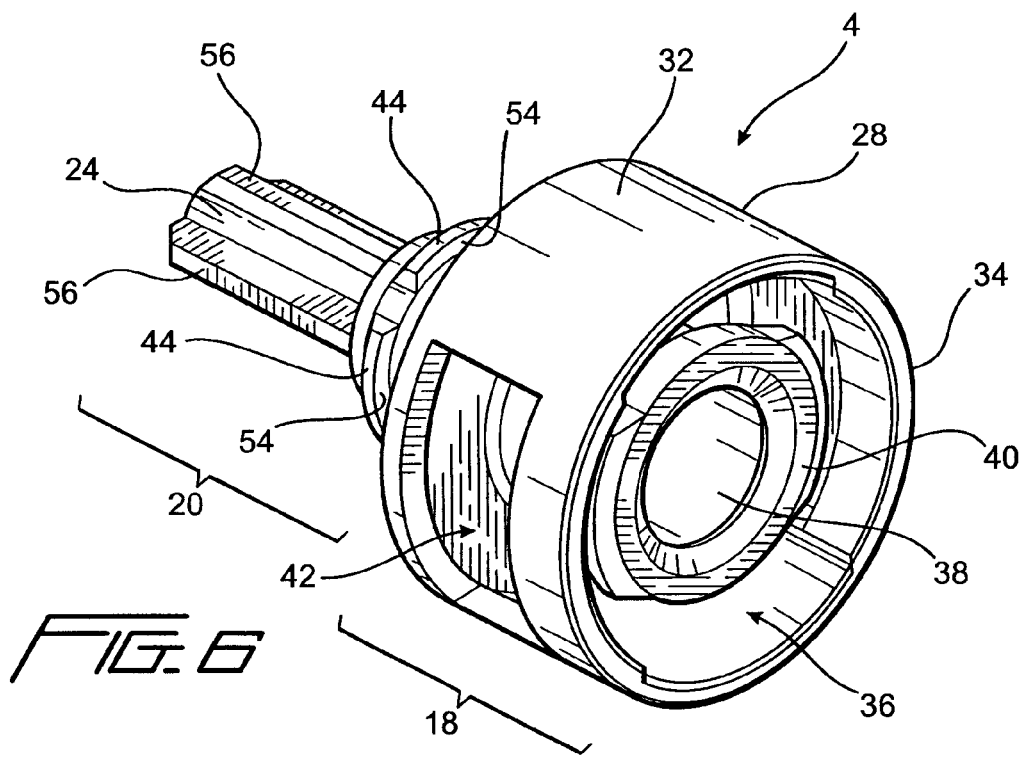
FIG. 6 is a perspective view of the needle hub of the safety needle assembly of the instant invention as viewed from its proximal end.
Figure 7:
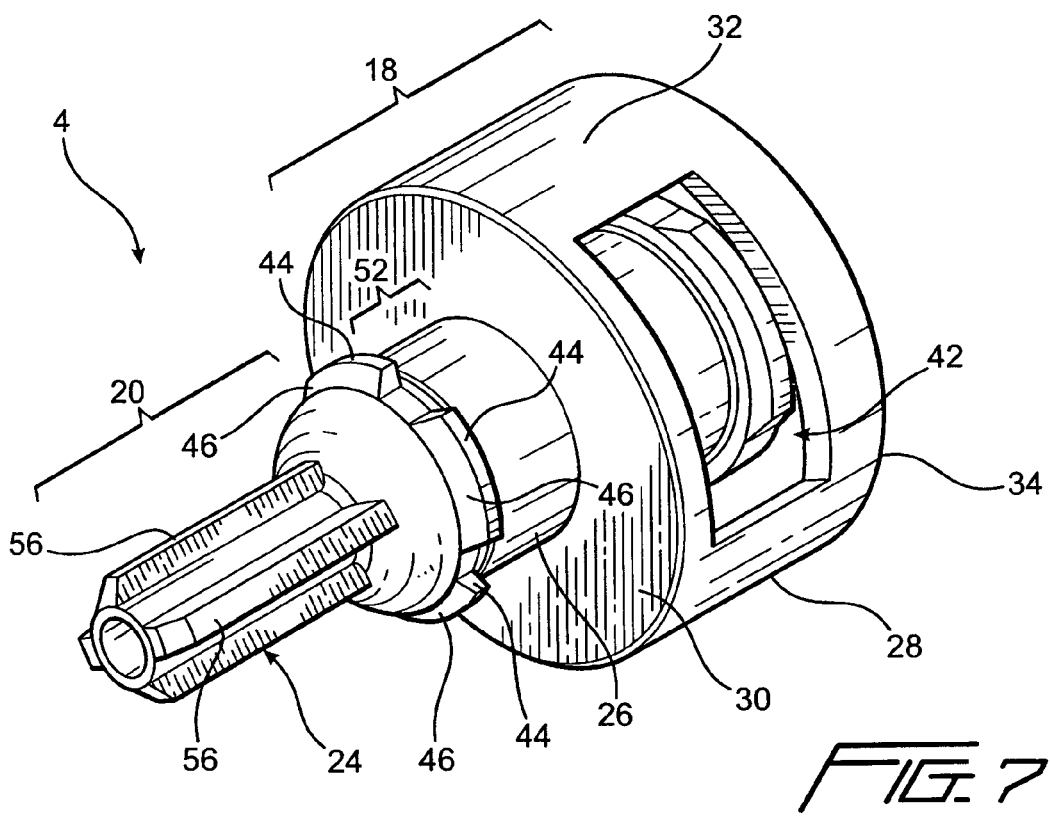
FIG. 7 is a perspective view of the needle hub of the instant invention safety needle assembly viewed from its distal end.
Figure 8:
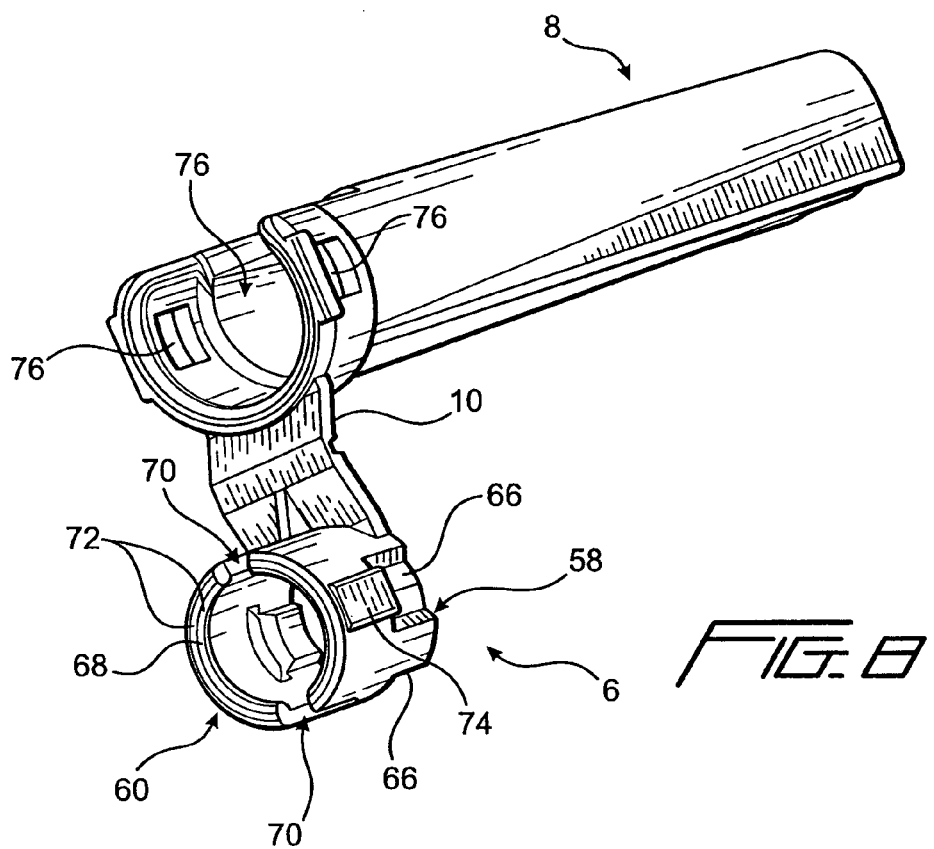
FIG. 8 is a perspective view of the needle protection housing and the collar to which it is attached.
Figure 9:
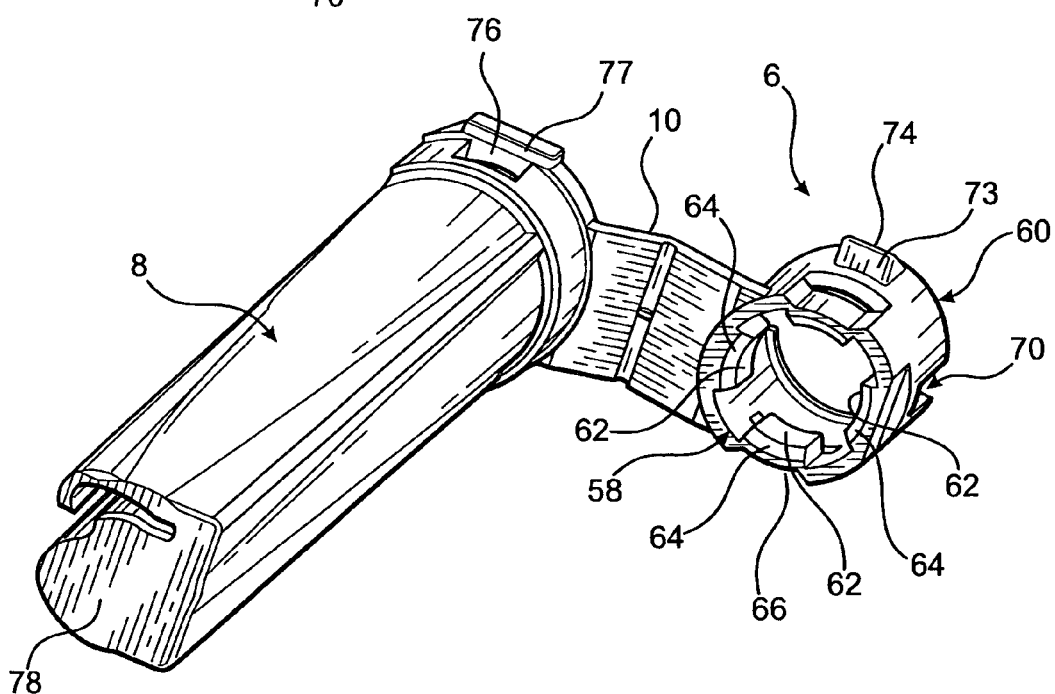
FIG. 9 is another perspective view of the FIG. 8 needle protection housing and collar.

With reference to FIGS. 1-5 and further with reference to FIGS. 6 and 7, needle hub 4 is shown to have a proximal portion 18 and a distal portion 20. For the sake of clarity, a needle 22 that fixedly extends from extension 24 of needle hub 4 is not shown in FIGS. 6 and 7. Further, it should be appreciated that proximal portion 18 and distal portion 20 of needle hub 4 do not have any actual line of demarcation, and are shown as such in FIGS. 4, 6 and 7 solely for the convenience of the reader.

As best shown in FIG. 6 and the cross-sectional views of FIGS. 4 and 5, needle hub 4 comprises a main body portion 26 that includes the base of needle hub 4. A ring 28 circumferentially surrounds the proximal portion of needle hub 4 in spaced relationship to main body portion 26. As shown, ring 28 is a part of needle hub 4 and is an integral part of main body portion 26 by means of a distal wall or partition 30 that extends transversely or orthogonally from main body portion 26. From distal wall 30 the sidewall 32 of collar 28 extends to a proximal end 34 that has an opening 36 formed concentrically with opening or cavity 38 at luer end 40 of needle hub main body portion 26. Since sidewall 32 of ring 28 is in spaced relationship with main body portion or base 26 of needle hub 4, luer end 40 of needle hub 4 accordingly is threadingly matable with a corresponding luer connector such as that shown for syringe 16 in FIG. 2.

Figure 2:
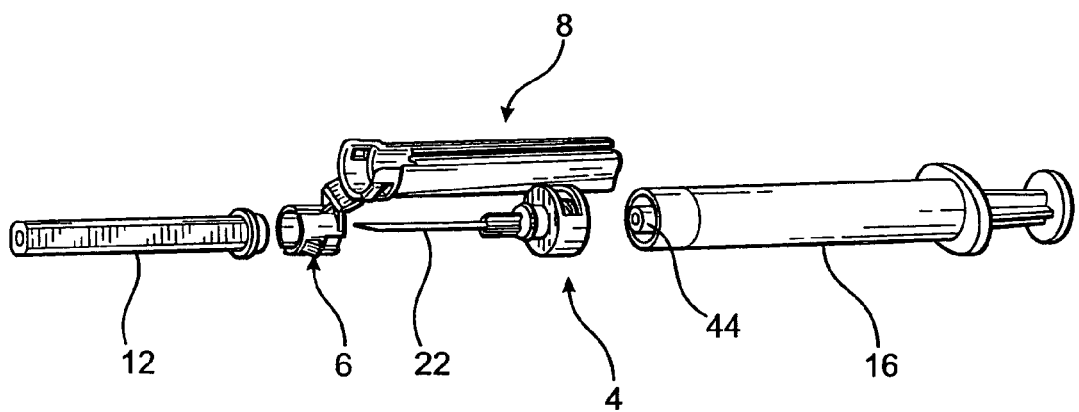

Ring 28 is also provided with two openings or windows 42 along its sidewall 32 to enable a user to view base portion 26 of needle hub 4. As needle hub 4, and the other components of the needle assembly, are made of conventional medical plastic such as polypropylene, or ABS plastic, and is substantially clear except for a color tinting as a way of color coding the assembly, the user can readily ascertain any flashing or blood, or blood flash, during a blood withdrawing procedure to thereby determine whether needle 22 has been correctly inserted into the vein of a patient. Thus, by way of windows 42, a user can view the base portion, as well as luer end 40 of needle hub 4. It should of course be appreciated that the safety needle assembly of the instant invention can also be used for infusion procedures. The dimension of ring 28 is such that it enables the user to readily grasp needle hub 4, and therefore the safety needle assembly as shown in FIG. 3, for mating to syringe 16 as shown in FIG. 2. As is well known, luer end 40 of needle hub 4 may be coupled to the corresponding luer end 44 of syringe 16 by a rotational movement when syringe 16 has a luer lock type receptacle, as shown in FIG. 2. Alternatively, in the case where the syringe has a luer slip type receptacle, the user, upon grasping ring 28, can simply insert luer 40 onto the luer slip receptacle of the syringe.

Further with respect to FIGS. 1-7 and in particular with respect to FIGS. 6 and 7, at the distal portion 20 of needle hub 4 there are provided a number of flanges 44 in a coaxially circumferential manner a predetermine distance from end wall 30 of ring 28. Flanges 44 each are chamfered or beveled at its front surface 46, and extend circumferentially proximate to the front end of cavity 38 of the base portion 26 of needle hub 4. As best shown in FIGS. 4 and 5, cavity 38 of base portion 26 is connected to needle 22 by a through bore 50 at extension 24. Extension 24 has a number of elongated ribs 56, which has no bearing for this invention other than for cosmetic and manufacturing processes not related to the instant invention, as ribs 56 do not come into contact with needle sheath 12 at any time. With flanges 44 extending from base portion 26 a predetermined distance from end wall 30, a space 52 is defined between flanges 44 and end wall 30 circumferentially about base portion 26. As best shown in FIG. 6, the back surfaces 54 of flanges 44 are formed at right angle to base portion 26.

As shown in FIGS. 1-5, needle hub 4 is in alignment with collar 6 and is coupled thereto per shown in the assembled views of FIGS. 3-5. In particular, with reference to FIGS. 8-11, collar 6 is pivotally connected to needle protection housing 8 by living hinge 10. As shown in FIG. 1, housing 8 is pivotable in the direction indicated by directional arrow 56, i.e., toward the longitudinal axis 14 for covering needle 22.

Collar 6 is cylindrical in shape and has a proximal portion or end 58 and a distal portion or end 60. There are formed at the inner surface at proximal portion 58 of collar 6 a plurality of protrusions 62 which are substantially rectangularly shaped. Protrusions 62 each may have a chamfered surface 64 that faces needle hub 4, as shown in the alignment of the components illustration of FIG. 1. Moreover, protrusion 62 are dimensioned such that when collar 6 is press-fitted to needle hub 4, they will matingly fit to space 52 defined by flanges 54 and end wall 30 at the distal portion of needle hub 4. The respective dimensions of space 52 and protrusions 62 may be such that, although collar 6 is rotatable about base portion 26 of needle hub 4, there nonetheless is enough friction between either one of flanges 44, end wall 30 or the outer surface of needle hub base 26 and protrusions 62 to render collar 6 not freely rotatable about needle hub 4, unless a predetermined torque or force is applied either to needle protection housing 8, living hinge 10 or collar 6, to rotate collar 6 relative to needle hub 4. Voids 66 provided at proximal portion 58 of collar 6 enable proximal portion 58 to flex, or expand, when collar 6 is press-fitted to the distal portion of needle hub 4, particularly when protrusions 62 come into contact with flanges 44. The respective chamfered or beveled surfaces 46 and 64 of flanges 44 and protrusions 62, respectively, facilitate the insertion of collar 6, and more particularly protrusions 62 into space 52 of needle hub 4.

Distal portion 60 of collar 6 has at its distal end, or proximate thereto, a rib 68 formed at the inner surface of collar 6. For the embodiment shown, rib 68 is divided into two halves, per notches 70 formed at opposed sides of distal portion 60. Notches 70 provide additional flexibility to the distal portion of collar 6 when needle sheath 12 is fitted thereto. More on that later. For now, it should be appreciated that rib 68 is formed to have either a semi-circular configuration or a configuration that is made up of a number of beveled surfaces for facilitating the mating of distal portion 60 of collar 6 with the proximal portion 74 of needle sheath 12. The beveled surfaces of rib 68 are collectively designated 72.

Needle protection housing 8 is connected, by living hinge 10, to collar 6 at the latter's proximal portion 58. Needle protective housing 8 has an open proximal end 75 and a closed end 78. Housing 8 is cylindrical in shape and has an opening 80 through which needle 22 passes, when housing 8 is pivoted toward collar 6 for covering needle 22 after needle sheath 12 has been removed from collar 6. Opening or channel 80 is formed by two lips or flaps 82 and 84 each of which extends longitudinally along the entire length of housing 8. Lip 82 overlaps lip 84, with the overlapping being such that the combination of lips 82 and 84 providing a trap door for needle 22. Thus, once needle 22 passes lips 82 and 84 into housing 8, it is trapped within housing 8 and is prevented from being further exposed.

Figure 10:
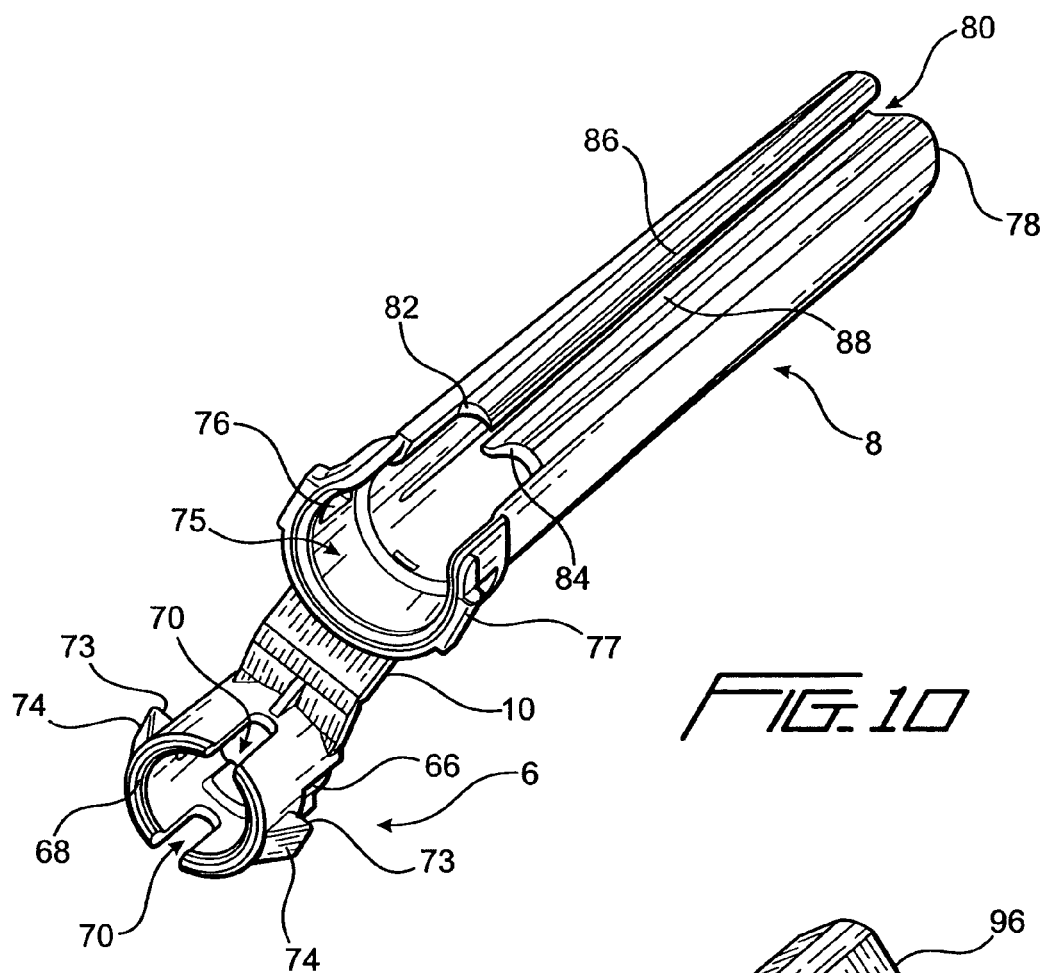
FIG. 10 is yet another view of the needle protection housing and collar of the instant invention safety needle assembly, with the lips that form the longitudinal slot along the housing clearly shown.

Opening 80, due to its formation by lips 82 and 84, is off-centered to one side of housing 8 to enhance the entry of needle 22 into housing 8. Each of lips 82 and 84 is angled, by a series of complex angles, as best shown in FIGS. 10 and 11, toward the interior of housing 8. The respective angles of each of the lips are therefore varied along the length of the housing for guiding needle 22 into housing 8 via opening 80. The respective progressively angled surfaces of lips 82 and 84 are designated 86 and 88, respectively. Given that the entry of needle 22 into housing 8 is guided by lips 82 and 84, the angled entry of needle 22 into housing 8 is effected in a smooth manner to substantially eliminate the possibility that contaminated fluid that remains on needle 22 after its use may be flickered or splattered when needle 22 comes into contact with housing 8.

To ensure that needle protection housing 8 remains fixedly retained along the longitudinal axis 14, a lock mechanism is provided at the proximal end 75 of needle housing 8 and the outer surface of collar 6. This ensures that once needle housing 8 is pivoted to the position along longitudinal axis 14, it will remain in alignment thereat. This lock mechanism, as shown in FIGS. 1-3 and 9-11, comprises two apertures 76 at the base of needle housing 8, and two corresponding one-way downward sloping catch members 74 at collar 6. Alternatively, as should readily be recognized, the apertures and catch members may be formed at collar 6 and the base of housing 8, respectively. Further, instead of apertures, non-through openings that nonetheless mate to the catch members are also envisioned. When needle protection housing 8 is pivoted to be in alignment along longitudinal axis 14, aperture 76 will snap fit over the one-way catch members 74, with the base surfaces 73 of the one-way catch members 74 acting against the top surfaces 77 at the base of apertures 76 to thereby fixedly retain needle housing 8 relative to collar 6.

Figure 12:
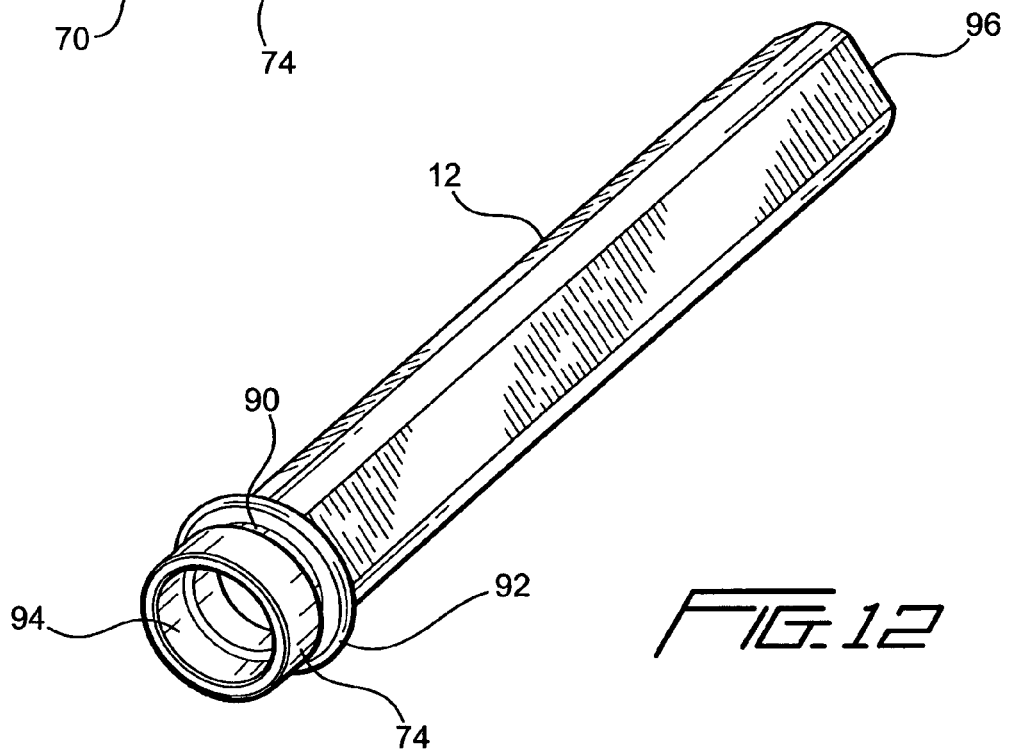
FIG. 12 is a perspective view of the needle sheath of the instant invention safety needle assembly as viewed from its open end.
Figure 13:
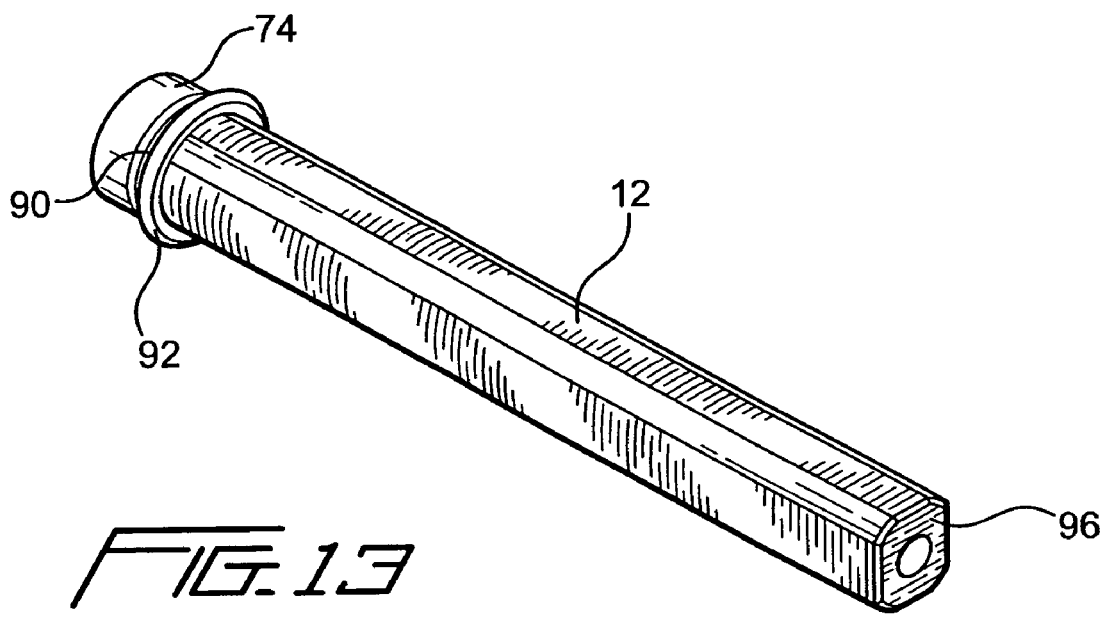
FIG. 13 is another perspective view of the needle sheath of FIG. 12 but viewed from its closed end.

As shown in FIGS. 12 and 13, needle sheath 12 has a first engage mechanism that engages to a second engage mechanism at collar 6. In particular, needle sheath 12 is a cylindrical cap that has formed at its proximal portion 74 a circumferential groove or slot 90. Groove 90 is configured to have a dimension, as defined by stop 92 and proximal portion 74, to accept rib 68 of collar 6. As shown, proximal portion 74 of needle sheath 12 has an opening 94 that allows needle sheath 12 to be placed or positioned over needle 22 and be press-fitted onto the distal end of collar 6. As the distal end of collar 6 has a rib 68 and opposed slots 70, when needle sheath 12 is fitted to collar 6, due to the elastic properties of the plastic material from which both collar 6 and needle sheath 12 are molded, the distal end of collar 6 would expand slightly so as to accept the proximal portion 74 of needle sheath 12, until rib 68 is snap fitted into groove 90, and the edge of the distal end of collar 6 rests against stop 92. Once snap fitted to collar 6, needle sheath 12 is removably engaged to collar 6. To remove needle sheath 12 from collar 6, a predetermined or greater force is applied to needle sheath 12 along longitudinal axis 14 for separating needle sheath 12 from collar 6. As best shown in FIG. 13, needle sheath 12 has a closed distal end 96.

In operation, with the assembled safety needle assembly as shown in FIG. 3, a user would remove needle sheath 12 by applying a predetermined force longitudinally relative to collar 6. Once exposed, needle 22 may be used. After use, needle protective housing 8 is pivoted to be in substantial alignment along longitudinal axis 14 so that the contaminated needle 22 enters into housing 8 and is trapped inside housing 8 by the trapdoor formed by lips 82 and 84. At the same time, housing 8 is fixedly retained to collar 6 by the mating of apertures 76 at the base of the housing 8 to the one-way catch member 74 at the outer surface of collar 6. To remove needle hub 4 from the syringe 28 of needle hub 4 is grasped, and in the case of a luer lock coupling, rotated counter-clockwise to remove needle hub 4 from the syringe, such as 16 shown in FIG. 2. Once removed from the syringe, the safety needle assembly could be properly disposed.

The invention claimed is:

1. Safety apparatus, comprising:
   a needle hub having a main body including a proximal portion and a distal portion, a needle extending from a distal end of said needle hub, said hub including a wall that extends orthogonally from the main body substantially at the junction where the proximal portion meets the distal portion;
   a collar having a proximal end rotatably mounted onto the distal portion of said needle hub so as to be rotatable about said needle hub, the wall at said hub providing a stop for the proximal end of said collar, said collar having a distal end and a second engage mechanism at the inner circumferential surface at the distal end;
   a housing pivotally connected to the proximal end of said collar; and
   a needle sheath having a proximal portion with a first engage mechanism at its outer circumferential surface, said first and second engage mechanisms fitted to each other when said sheath is fitted to the distal end of said collar, said proximal portion of said needle sheath being in contact engagement to said collar but not in contact with said needle hub for covering said needle extending from the distal end of said needle hub when said sheath is fitted to said collar and said first and second engage mechanisms are engaged to each other.

2. Safety apparatus of claim 1, wherein after said needle sheath is removed from said collar, said housing is pivotable to a position substantially in alignment along a longitudinal axis of said needle hub for covering said needle.

3. Safety apparatus of claim 1, wherein said first engage mechanism of said needle sheath comprises a groove formed circumferentially proximate to the open end of sad needle sheath and wherein said second engage mechanism of said collar comprises a rib circumferentially formed at the inner wall of the distal end of said collar; and
wherein said needle sheath is attached to said collar when said rib of said collar mates with said groove after said needle sheath is positioned over said needle and engages said collar.

4. Safety apparatus of claim 1, wherein said needle hub comprises a luer end at its proximal portion, a ring surrounding and spaced from said luer end, said ring being integrally connected to the wall extending transversely the main body of said hub; and
wherein a user can readily grasp said ring to couple said safety device to a medical device by threadingly mating said luer end of said needle hub to a counterpart luer end at said medical device.

5. Safety apparatus of claim 4, wherein said ring comprises at least one window along its sidewall to enable the user to view said luer end of said needle hub and said needle hub.

6. Safety apparatus of claim 1, wherein said needle hub comprises at least one flange extending from its distal portion, said flange being located a predetermined distance from the wall projecting orthogonally from said needle hub, a space being formed between said flange and said wall circumferentially about said needle hub; and
wherein said collar comprises at least one protrusion at the inner wall of its proximal portion, said protrusion being dimensioned to fit to said space defined between said flange and said wall when said collar is mated to said needle hub, said collar rotatable about said needle hub after matingly fitted to said space.

7. Safety apparatus of claim 1, wherein said housing comprises a longitudinal opening formed by first and second lips each extending along substantially the length of said housing, said first lip overlapping a portion of said second lip with said opening being off centered from said longitudinal axis, each of said lips being angled toward the interior of said housing with the respective angles of said lips being varied along the length of said housing to effect a guide for said needle to smoothly enter into said housing at an angle through said opening when said housing is pivoted to cover said needle, said needle not removable from said housing once said needle fully enters into said housing.

8. Safety apparatus of claim 1, wherein said collar has formed proximate to its distal end one lock mechanism and wherein said housing has formed at its proximal end an other lock mechanism, said one and other lock mechanisms coacting to fixedly retain said housing to said collar once said housing is pivoted to a position in substantial alignment with said needle hub to cover said needle.

9. Safety apparatus of claim 8, wherein said one lock mechanism comprises at least one way catch member extending from the outer surface of said collar or said housing, and said other lock mechanism comprises at least one corresponding aperture at said housing or said collar, said one way catch member matingly coupled to said aperture for fixedly retaining said housing to said collar when said housing is pivoted to cover said needle.

10. In combination, a needle hub having a main body including a proximal portion and a distal portion, said proximal portion having a luer connector and a ring in the form of a circumferential sidewall surrounding but in spaced relationship with said luer connector, said ring being an integral part of said hub and is connected to a wall that extends orthogonally from the main body substantially at the junction where the proximal and distal portions of said needle hub meet, at least one window provided along the sidewall at said ring to enable viewing of said luer connector, said ring being graspable by a user to remove said needle hub from a syringe, said distal portion of said needle hub having a distal end from which a needle extends, a collar having a proximal end and a housing pivotally connected to the proximal end fitted to and rotatable about said distal portion of said needle hub, and a needle sheath having a proximal portion in contact engagement to the distal end of said collar but not in contact with said needle hub when said sheath is fitted to said collar, said sheath removable from said collar to expose said needle for use.

11. Combination of claim 10, wherein said needle sheath comprises a first engage mechanism proximate to its open end and wherein said collar comprises a second engage mechanism at its distal portion, said first engage mechanism engages said second engage mechanism for attaching said needle sheath to said collar when said needle sheath is positioned over said needle and mates with said collar.

12. Combination of claim 10, wherein said needle sheath comprises a circumferential groove proximate to its open end and said collar comprises a circumferential rib at its distal portion, said rib mating to said groove when said needle sheath is positioned over said needle and fitted to said collar.

13. Combination of claim 10, wherein said ring comprises at least one window on its sidewall to enable viewing of said luer connector and said proximal portion of said needle hub.

14. Combination of claim 10, wherein said ring is adaptable to be used by a user to grasp said needle hub for connecting said luer connector to a corresponding luer connector of a medical device.

15. Combination of claim 10, wherein said needle hub comprises a plurality of flanges extending from its distal portion, said flanges being located a predetermined distance from the wall projecting orthogonally from said needle hub, a space being defined between said flanges and said wall circumferentially about said needle hub, and wherein said collar comprises a plurality of protrusions at the inner wall of its proximal portion, said protrusions being dimensioned to fit to said space when said collar is mated to said needle hub, said collar rotatable about said needle hub after matingly fitted to said space.

16. Combination of claim 10, wherein said housing comprises a longitudinal opening formed by first and second lips each extending along substantially the length of said housing, said first lip overlapping a portion of said second lip with said opening being off centered from said longitudinal axis, each of said lips being angled toward the interior of said housing with the respective angles of said lips being varied along the length of said housing to effect a guide for said needle to smoothly enter into said housing at an angle through said opening when said housing is pivoted to cover said needle, said needle not removable from said housing once said needle fully enters into said housing.

17. Combination of claim 10, wherein said collar has formed proximate to its distal end a first lock mechanism and wherein said housing has formed at its proximal end a second lock mechanism, said first and second lock mechanisms coacting to fixedly retain said housing to said collar once said housing is pivoted to a position in substantial alignment with said needle hub to cover said needle.

18. A method of making a needle assembly, comprising the steps of:
- a) providing a needle hub having a main body including a proximal portion and a distal portion, said hub including a wall that extends orthogonally from the main body at the junction where the proximal and distal portions meet;
- b) fixedly attaching a needle to a distal end of said needle hub;
- c) pivotally connecting a housing to a proximal end of a collar having a distal end and a second engage mechanism formed at the inner circumferential surface at the distal end;
- d) rotatably mounting the proximal end of said collar onto the distal portion of said needle hub so that said collar is rotatable about said needle hub, the wall at said hub providing a stop for the proximal end of said collar; and
- e) fitting a needle sheath having a first engagement mechanism at the circumferential outer surface at its proximal portion to the distal end of said collar, said first and second engage mechanisms fitting to each other so that said sheath is removably engaged to said collar, the proximal portion of said needle sheath being engaged to said collar without said needle sheath contacting said needle hub for covering said needle extending from the distal end of said needle hub.

19. Method of claim 18, further comprising the steps of:
removing said needle sheath from said collar before using said needle; and
pivoting said housing to a position substantially in alignment along a longitudinal axis of said needle hub for covering said needle.

20. Method of claim 18, wherein said first engage mechanism comprises a circumferential groove formed proximate to an open end of said needle sheath, and wherein said second engage mechanism comprises a rib formed circumferentially at the inner wall of a distal portion of said collar; and
wherein said step e comprises the steps of:
positioning said needle sheath over said needle; and
engaging said needle sheath to said collar until said rib of said collar mates with said groove of said needle sheath.

21. Method of claim 18, wherein said step a comprises the steps of:
forming a luer end at the proximal portion of said needle hub; and
forming a ring in spaced relation to surround said luer end, said ring being integral of said needle hub via a distal end wall;
wherein a user can readily grasp said ring to couple said needle assembly to a medical device by mating said luer end of said needle hub to a counterpart luer end at said medical device.

22. Method of claim 18, wherein said forming a ring step further comprises the step of:
forming at least one window on said ring to enable the user to view said luer end of said needle hub and said needle hub.

23. Method of claim 18, wherein said step a comprises the steps of:
providing at least one flange extending from said distal portion of said needle hub; and
locating said flange a predetermined distance from the wall projecting orthogonally from said needle hub to define a space between said flange and said wall circumferentially about said needle hub;
wherein the method further comprising the steps of:
forming at least one protrusion at the inner wall of said collar;
dimensioning said protrusion to fit to said space defined between said flange and said wall; and
mating said collar to said needle hub, said collar rotatable about said needle hub after being mated to said space.

24. Method of claim 18, further comprising the step of:
providing a longitudinal opening along said housing by forming first and second lips each extending along substantially the length of said housing, said first lip overlapping a portion of said second lip with said opening being off centered from said longitudinal axis, each of said lips being angled toward the interior of said housing with the respective angles of said lips being varied along the length of said housing to effect a guide for said needle to smoothly enter into said housing at an angle through said opening when said housing is pivoted to cover said needle, said needle not removable from said housing once said needle fully enters into said housing.

25. Method of claim 18, further comprising the steps of:
forming a first lock mechanism proximate to the distal end of said collar; and
forming a second lock mechanism at a proximal end of said housing;
wherein said first and second lock mechanisms coact to fixedly retain said housing to said collar once said housing is pivoted to a position in substantial alignment with said needle hub to cover said needle.

* * * * *